United States Patent
Metelski

(10) Patent No.: US 6,947,211 B2
(45) Date of Patent: Sep. 20, 2005

(54) SURGICAL MICROSCOPE

(75) Inventor: Andrzej Metelski, Romanshorn (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 10/288,792

(22) Filed: Nov. 6, 2002

(65) Prior Publication Data
US 2003/0090790 A1 May 15, 2003

(30) Foreign Application Priority Data
Nov. 13, 2001 (DE) .......................... 101 55 719

(51) Int. Cl.[7] .............................................. G02B 21/00
(52) U.S. Cl. ..................... 359/384; 359/368; 359/372; 359/392; 359/393
(58) Field of Search ................. 357/384, 383, 357/368, 372, 382, 391, 392, 393, 394

(56) References Cited

U.S. PATENT DOCUMENTS

| | | | | |
|---|---|---|---|---|
| 4,589,741 A | * | 5/1986 | Clegg | 359/394 |
| 4,627,009 A | * | 12/1986 | Holmes et al. | 700/302 |
| 5,748,366 A | * | 5/1998 | Yasunaga et al. | 359/368 |
| 5,825,536 A | * | 10/1998 | Yasunaga et al. | 359/384 |
| 5,861,983 A | | 1/1999 | Twisselman | |

FOREIGN PATENT DOCUMENTS

| | | |
|---|---|---|
| DE | 4226608 A1 | 2/1993 |
| DE | 42 14 858 C1 | 2/1994 |
| DE | 4416178 A1 | 12/1994 |
| EP | 0700665 B1 | 3/1996 |
| EP | 0791339 A1 | 8/1997 |
| GB | 1431653 A | 4/1976 |
| JP | 53087247 A | 8/1978 |
| JP | 09224956 A | 9/1997 |
| WO | WO 97/13997 | 4/1997 |

* cited by examiner

*Primary Examiner*—Drew A. Dunn
*Assistant Examiner*—Joshua L Pritchett
(74) *Attorney, Agent, or Firm*—Hodgson Russ LLP

(57) ABSTRACT

The invention concerns a surgical microscope having a stand and having an optics carrier (7a) joined movably to the stand and mounted movably with respect to the stand. The optics carrier (7a) is mounted, in the region of its center of gravity, pivotably about at least one axis (17a) with respect to a pivot support (6a) of the stand. At least one of the pivot axes (17a) is constituted virtually by the center of an arc-segment-shaped guidance element (10a) that coacts with a guide carriage (11a).

11 Claims, 2 Drawing Sheets

SURGICAL MICROSCOPE

CROSS REFERENCE TO RELATED APPLICATIONS

This application claims priority of the German patent application 101 55 719.1 filed Nov. 13, 2001 which is incorporated by reference herein.

FIELD OF THE INVENTION

The invention concerns a surgical microscope having a stand and having an optics carrier joined movably to the stand and mounted movably with respect to the stand, the optics carrier being mounted, in the region of its center of gravity, pivotably about at least one axis with respect to a pivot support of the stand.

BACKGROUND OF THE INVENTION

Surgical microscopes must be very movable and must be quickly adjustable without great energy expenditure. To ensure that the microscope does not shift by itself once a position has been established, the forces and moments occurring in each location must be equalized. If they are not equalized, brakes or bracing devices must then be present; these in turn disadvantageously increase the overall weight without optimally balancing (hysteresis). Even if brakes are present, however, the forces and moments should be equalized in order to permit "feather-light" movement of the microscope when the brakes are released.

When in use, surgical microscopes are utilized with a wide variety of different accessories (e.g. tubes, extensions, filters, lens attachments, etc.). In many cases, however, these accessories result in a displacement of the overall center of gravity. As a result, the system is no longer in equilibrium and must be balanced out again. This balancing can be accomplished, for example, by attaching, removing, or shifting additional counterweights. This method is very time-consuming, however, and also creates elevated forces and moments at the stand.

DE 42 14 858 C1 discloses a stand for a medical X-ray device that carries a C-shaped arc. An X-ray source is arranged at one end of the arc, and an image intensifier at the other end.

Also known is an optics carrier that is pivot-mounted on the pivot support on only one side (to the left of the microscope). The region of the axis at the center of gravity to the right of the microscope is thus unoccupied, so that accessories or additional devices can be installed there. Disadvantageously, the left-side attachment eliminates the possibility of mounting accessories there as well.

SUMMARY OF THE INVENTION

It is the object of the invention to create an apparatus that allows the surgical microscope to be balanced out easily and quickly and that avoids the disadvantages of the known approaches, in particular the installation of additional weights or single-side attachments.

This object is achieved, according to the present invention, by using an arc-segment-shaped guidance element arranged to guide rotation of an optics carrier of the microscope relative to a pivot support connected to the microscope stand. The arc-segment-shaped guidance element has a virtual central axis, wherein the pivot axis of the optics carrier coincides with the central axis of the guidance element.

The actual guidance system of the optics carrier is thus located outside the virtual pivot axis. Since the center of gravity of the optics carrier is often located in the vicinity of the optical system, it is thus possible to place the virtual pivot axis exactly in the center of gravity of the optics carrier without thereby adversely affecting the optical system with real shafts or the like. This allows additional devices to be connected to the microscope even in the vicinity of the axis—and moreover on both sides of the microscope—with no need to install an additional counterweight (additional weight) on the optics carrier. The overall weight of the optics carrier is thus reduced as compared to the known configuration of the applicant's optics carrier (WO 97 13997 A1). A consequence of this is a reduction in the overall inertia and weight of the entire assemblage. This results in smooth adjustability.

The arc-segment-shaped guidance element advantageously coacts with a guide carriage or guide cage. These two elements together form the actual guidance system. The guidance clearance necessary for relative mobility can, for example, be defined by fabrication tolerances or can be adjustable.

An advantageous embodiment of the invention consists in the fact that the arc-segment-shaped guidance element is connected to the optics carrier displaceably in at least one spatial axis. This connection can be accomplished via an intermediate member.

In the initial position of the optical carrier, the axis can extend horizontally or vertically.

Displacement of the arc-segment-shaped guidance element is advantageously accomplished by way of linear slides. These slides enable accurate guidance and are capable of absorbing forces and also any tilting moments that may occur.

If the accessory on the microscope is changed, the overall center of gravity of the optics carrier very often shifts at least two-dimensionally. Two slides arranged substantially perpendicular to one another are therefore advantageously provided in order to balance out the system. Displacement of the arc-segment-shaped guidance element and thus also of the virtual axis is therefore possible. The virtual axis can thus easily be placed in the center of gravity of the optics carrier.

For rapid and precise balancing of the optics carrier, displacement of the arc-segment-shaped guidance element is advantageously accomplished by means of threaded spindles. These threaded spindles are preferably self-locking. Additional clamping is therefore usually not necessary.

Also within the context are motorized drives for the threaded spindles, which also can be remotely controlled and/or regulated by means of an automatic control system.

In a system that is not balanced out, for example during an accessory change, greater forces and torques can occur at the arc-segment-shaped guidance element. In order to handle these at least partially, a brake system is provided on the arc-segment-shaped guidance element. The brake system can be entirely or partially releasable for displacement of the optics carrier.

The brake system advantageously comprises lockable pincers that coact with the arc-segment-shaped guidance element. Pincers of this kind can fit around the guidance element on both sides (as in the case of a disk brake), and immobilize it when necessary. Other braking devices, including linear ones, are also within the purview of the invention.

To ensure that the microscope is not inadvertently displaced by gentle contact, but on the other hand that its position can be modified if necessary even with the brake applied, the brake system exhibits a controllable and adjustable braking force. This braking force can be generated by spring elements, electromagnets, or a combination of the two.

For reasons of statics, the arc-segment-shaped guidance element should usually be arranged in a plane that is located outside the overall center of gravity and extends perpendicular to the axis. This can in some cases cause tilting moments that could have a negative effect on the stability of the system. To eliminate such tilting moments, according to a development of the invention two arc-segment-shaped guidance elements, arranged parallel to one another, are provided for each pivot axis. Alternatively or additionally, a displacement device for the optics carrier that makes the optics carrier shiftable laterally along the axis (Y displacement) can also be provided.

The friction of the guidance elements should be low in order to permit smooth displacement of the microscope. It is therefore advisable for the guidance element to be embodied as a curved ball guidance slide. Ball guidance slides of this kind function in principle like rolling bearings, and have very low rolling resistance. Commercially available bearing elements can preferably be used for this purpose. If, on the other hand, a certain baseline friction should be desired because of its braking effect, a plain-bearing guidance system can be used instead of rolling bearings.

Two guidance elements arranged parallel to one another are preferably provided. This minimizes the stress on the individual guidance elements due to forces and moments that occur.

BRIEF DESCRIPTION OF THE DRAWINGS

The invention is presented in exemplary embodiments and will be explained in more detail with the aid of the schematic drawings that follow, in which.

DETAILED DESCRIPTION OF THE INVENTION

Figure 1:
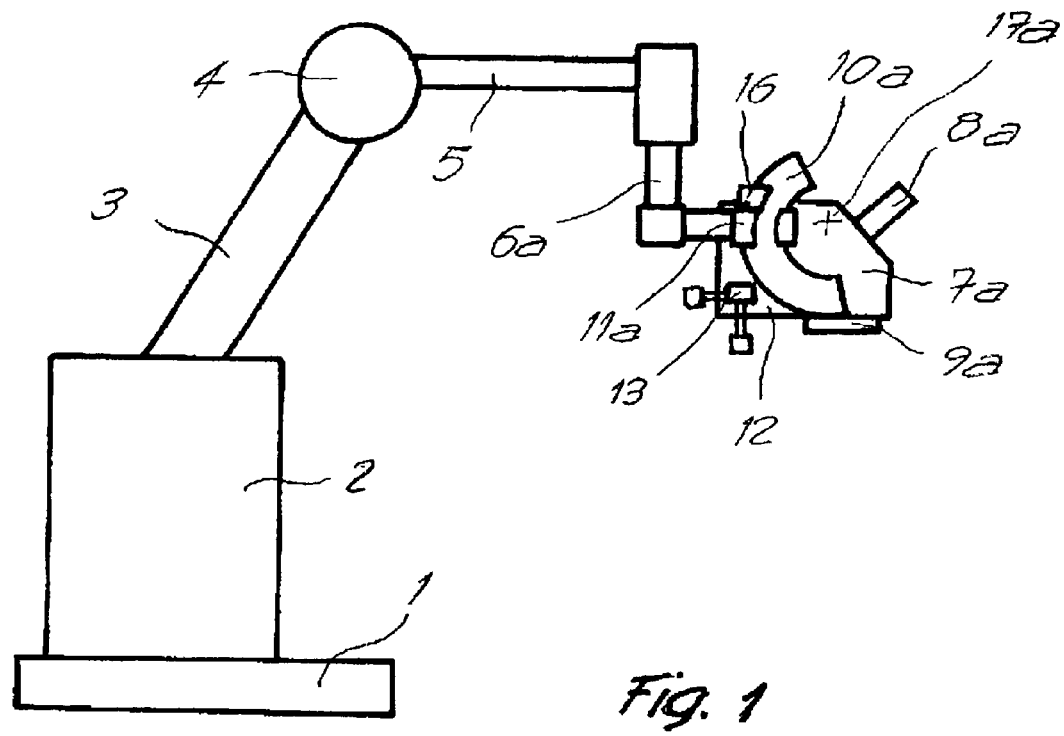
FIG. 1 shows a surgical microscope according to the present invention, having a stand.

The surgical microscope visible in FIG. 1 comprises a stand that is substantially made up of a stand foot 1, a stand column 2, and an extension arm 3 mounted in stand column 2. A carrier arm 5 is connected via a joint 4 to extension arm 3. Suspended at the free end of carrier arm 5 is a pivot support 6a that is movable in a horizontal plane. An optics carrier 7a is joined, movably in multiple axes, to pivot support 6a. A tube 8a and an objective 9a are depicted on optics carrier 7a as examples of exchangeable accessories.

The term "stand" for purposes of the invention is to be understood to mean all retaining systems that retain a pivot support movably with respect to its surroundings; this applies, for example, to wall, floor, and ceiling mounts. The configuration of the stand is not significant for the invention.

Optics carrier 7a is joined to pivot support 6a by way of an arc-segment-shaped guidance element 10a and a guide carriage 11a coacting therewith. In this exemplary embodiment, guidance element 10a is joined to optics carrier 7a, and guide carriage 11a to pivot support 6a. In principle, however, this can also be exactly the opposite.

Figure 2:
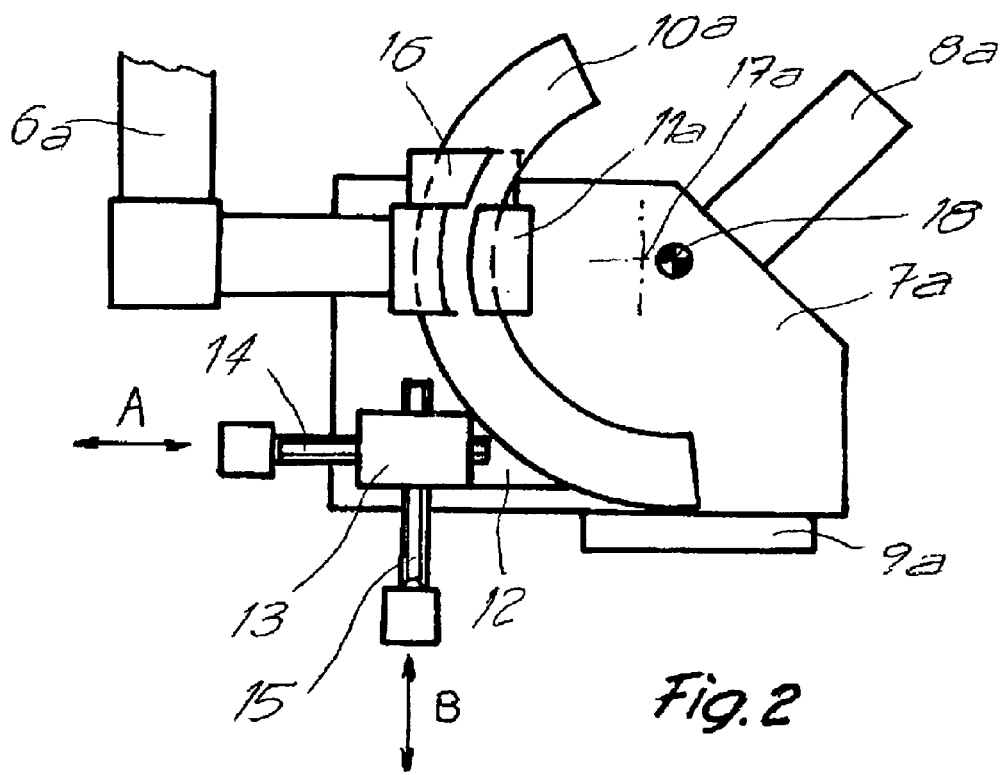
FIG. 2 shows a portion of the microscope depicted in FIG. 1 at enlarged scale.

By way of an A–B slide 12, 13 arranged between optics carrier 7a and arc segment 10a (FIG. 2), guidance element 10a can be displaced with respect to optics carrier 7a by means of threaded spindles 14, 15. As a variant, the A-B slide can also be arranged between guide carriage 11 and pivot support 6a.

The pivoting of optics carrier 7a with respect to pivot support 6a is regulated by means of an adjustably configured brake 16 that acts on arc-segment-shaped guidance element 10a.

Displacement of arc-segment-shaped guidance element 10a with respect to optics carrier 7a causes the (virtual) pivot axis 17a to be shifted into center of gravity 18 of optics carrier 7a. Optics carrier 7a is thereby brought into a balanced equilibrium position so that it can be smoothly pivoted into any desired position and will then remain there.

Figure 3:
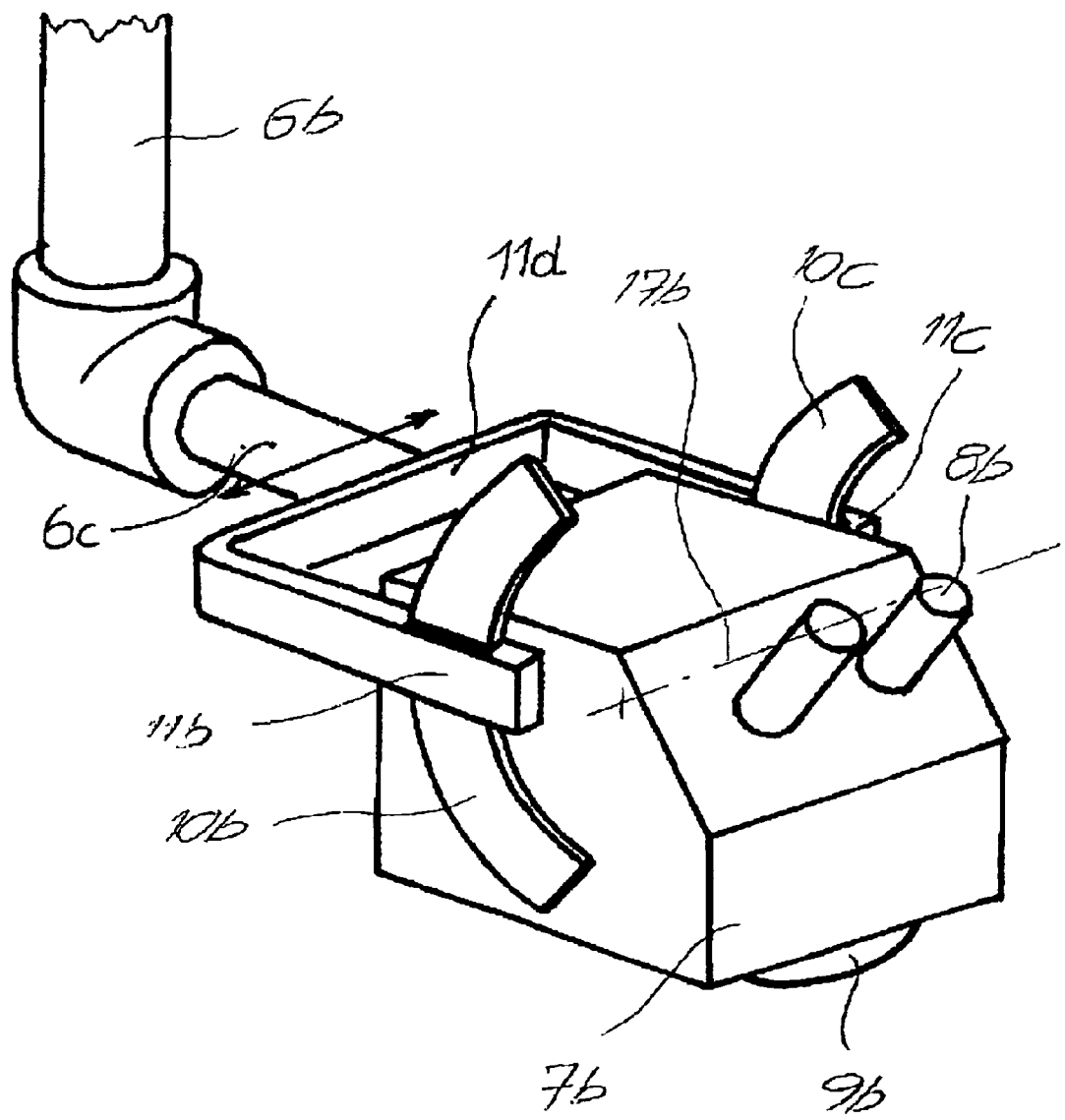
FIG. 3 shows a variant of the microscope having two guidance elements arranged parallel to one another.

In the exemplary embodiment of FIG. 3, two arc-segment-shaped guidance elements 10b, 10c are arranged parallel to one another. Optics carrier 7b has a tube 8b and an objective 9b, and is mounted on guide carriages 11b, 11c, via guidance elements 10b, 10c, between the limbs of pivot carrier 6b that is configured at its free end as a fork. This arrangement has substantial advantages over single-side mounting, since bearing forces are reduced. Guidance elements 10b, 10c can be configured as plain-bearing or rolling-bearing elements. Using a displacement mechanism analogous to that depicted in FIG. 2, pivot axis 17b can be shifted into the center of gravity of the optics carrier so that the latter can be moved without great energy expenditure into any desired position and will then remain there. A Y-direction displacement (along pivot axis 17a,b) is made possible by a displacement device (not depicted in further detail), known per se, between a pivot support part 6c and a guidance system part 11d (see arrow).

| PARTS LIST | |
|---|---|
| 1 | Stand foot |
| 2 | Stand column |
| 3 | Extension arm |
| 4 | Joint |
| 5 | Carrier arm |
| 6a, b, c | Pivot support |
| 7a, b | Optics carrier |
| 8a, b | Tube |
| 9a, b | Objective |
| 10a, b, c | Arc-segment-shaped guidance element |
| 11a, b, c, d | Guide carriage |
| 12 | A-slide |
| 13 | B-slide (A-B slide in a horizontal and vertical direction) |
| 14 | Threaded spindle |
| 15 | Threaded spindle |
| 16 | Brake |
| 17a, b | Pivot axis |
| 18 | Center of gravity |

What is claimed is:

1. A surgical microscope comprising:

a stand;

a pivot support connected to said stand and movable relative to said stand;

an optics carrier connected to said pivot support, said optics carrier being rotatable relative to said pivot support about a horizontal pivot axis, said optics carrier including a center of gravity at a location determined by said optics carrier and any optics carried thereby;

a guide carriage for connecting said optics carrier to said pivot support; and an arc-segment-shaped guidance element arranged to guide said rotation of said optics carrier relative to said pivot support, said arc-segment-shaped guidance element having a virtual central axis, wherein said pivot axis of said optics carrier coincides with said central axis of said arc-segment-shaped guidance element and said arc-segment-shaped guidance element coacts with said guide carriage to guide said rotation of said optics carrier about said pivot axis, and wherein said arc-segment-shaped guidance element is connected to said optics carrier to permit relative displacement between said arc-segment-shape guidance element and said optics carrier to allow said center of gravity to be aligned with said pivot axis.

2. The surgical microscope as defined in claim 1, wherein said arc-segment-shaped guidance element is connected to said optics carrier to permit relative displacement between said arc-segment-shaped guidance element and said optics carrier along at least one spatial axis, said displacement being independent of said rotation of said optics carrier about said pivot axis.

3. The surgical microscope as defined in claim 2, wherein said arc-segment-shaped guidance element is connected to said optics carrier by a pair of linear slides enabling relative displacement between said arc-segment-shaped guidance element and said optics carrier along perpendicular displacement axes.

4. The surgical microscope as defined in claim 3, wherein said pair of linear slides include each include a threaded spindle for causing displacement.

5. The surgical microscope as defined in claim 1, further comprising a brake system arranged to act on said arc-segment-shaped guidance element to brake rotation of said optics carrier about said pivot axis at a chosen rotational position.

6. The surgical microscope as defined in claim 5, wherein said brake system includes lockable pincers that coact with said arc-segment-shaped guidance element.

7. The surgical microscope as defined in claim 5, wherein said brake system applies a controllable and adjustable braking force.

8. The surgical microscope as defined in claim 1, wherein said guidance element is a curved ball guidance slide.

9. The surgical microscope as defined in claim 1, wherein said guidance element is a curved plain guidance system.

10. The surgical microscope as defined in claim 8, wherein two said guidance elements arranged in parallel planes spaced apart along said pivot axis are provided.

11. The surgical microscope as defined in claim 9, wherein two said guidance elements arranged in parallel planes spaced apart along said pivot axis are provided.

* * * * *